United States Patent [19]

Zhang

[11] Patent Number: 5,763,282
[45] Date of Patent: Jun. 9, 1998

[54] ABSORBANCE ASSAY FOR THE MEASUREMENT OF CORNIFIED ENVELOPES USING BICINCHONINIC ACID

[75] Inventor: Kelly Hua Zhang, Piscataway, N.J.

[73] Assignee: Chesebrough-Pond's USA Co., Division of Conopco, Inc., Greenwich, Conn.

[21] Appl. No.: 821,152

[22] Filed: Mar. 20, 1997

[51] Int. Cl.$^6$ .................................................. G01N 33/68
[52] U.S. Cl. .............................. 436/86; 436/164; 436/178
[58] Field of Search .................................. 436/63, 86, 164, 436/166, 178

[56] References Cited

U.S. PATENT DOCUMENTS

| | | | |
|---|---|---|---|
| 4,839,295 | 6/1989 | Smith | 436/86 |
| 5,506,144 | 4/1996 | Sundrehagen | 436/66 |
| 5,654,171 | 8/1997 | Suginaka et al. | 435/69.1 |

OTHER PUBLICATIONS

Monroe et al., "Quantitation of Cross–Linked Protein: An Alternative to Counting Cornified Envelopes as an Index of Keratinocyte Differentiation", Analytical Biochemistry, 199, pp. 25–28 (1991).

Lowry et al., "Protein Measurement With The Folin Phenol Reagent", Washington University School of Medicine, St. Louis, Missouri, May 28, 1951, pp. 265–275.

Sun et al., "Differentiation of the Epidermal Keratinocyte in Cell Culture: Formation of the Cornified Envelope", Cell, vol. 9, pp. 511–521, Dec. 1975(Part 1).

Stich, "Determination of Protein Covalently Bound to Agarose Supports Using Bicinchoninic Acid", Analytical Biochemistry, 191, pp. 343–346 (1990).

Smith et al., "Measurement of Protein Using Bicinchoninic Acid", Analytical Chemistry, 150, pp. 76–85 (1985).

Hill et al., "Protein Determination Using Bicinchoninic Acid in the Presence of Sulfhydryl Reagents", Analytical Biochemistry, 170, pp. 203–208 (1988).

Pierce Chemical Company, Product Brochure Instructions, "BCA Protein Assay Reagent Kit", USA, Jun. 1996.

Pierce Chemical Company, Product Brochure Instructions, "BCA Protein Assay Reagent", USA, Jul. 1995.

*Primary Examiner*—Jeffrey Snay
*Attorney, Agent, or Firm*—Rimma Mitelman

[57] ABSTRACT

A rapid, practical assay for measuring the concentration of cornified envelopes based on measuring the absorbance, which utilizes the addition of bicinchoninic acid to insoluble cornified envelopes preparation, after the cornified envelopes have been separated from soluble proteins.

3 Claims, No Drawings

ABSORBANCE ASSAY FOR THE MEASUREMENT OF CORNIFIED ENVELOPES USING BICINCHONINIC ACID

FIELD OF THE INVENTION

The present invention is directed to an absorbance-based method for measuring the concentration of cornified envelopes, which utilizes the addition of BCA to cornified envelopes preparation, after the removal of soluble proteins from the cornified envelopes preparation.

BACKGROUND OF THE INVENTION

The top layer of human skin or the epidermis is composed of many different cell types including keratinocytes, melanocytes and langerhans cells. Keratinocytes are the major cell type of the epidermis (75–80% of the total number of cells in the human epidermis). Within the epidermis the keratinocytes reside in four distinct stages of differentiation. The basal layer rests on the basal lamina separating epidermis from the dermis. These cells are large columnar rapidly proliferating cells. These basal cells migrate upward within the epidermis, initiated by the process of differentiation. The layer above the basal cells is the spinous layer. The cells in the spinous layer initiate the production of proteins characteristic of the differentiated epidermis. The granular layer, lying above the spinous layer, is characterized by electron-dense granules. This layer is responsible for the synthesis of lipid molecules required for the formation of the water impermeable barrier of the skin. The topmost layer of the skin, the stratum corneum, is formed from the granular layer by the destruction of cellular organelles. The cells in the stratum corneum, corneocytes, contain extensively cross-linked proteins, surrounded by a highly resistant cell envelope. These cross-linked proteins surrounded by a cell envelope are known as "cornified envelopes".

The cornified envelopes (CE) are composed of numerous distinct proteins which have been cross-linked together by the formation of $N^\epsilon$-($\gamma$-glutamyl) lysine isodipeptide bonds catalyzed by the action of at least two different transglutaminases expressed in the epidermis. Transglutaminase-1 (TG-1) is expressed in abundance in the differentiated layers of the epidermis, especially the granular layer, but is absent in the undifferentiated basal epidermis. Thus, TG-1 is a useful marker of epidermal keratinocyte differentiation with high TG-1 levels indicating a more differentiated state. An ELISA based TG-1 assay, using a TG-1 antibody has been used to assess the state of differentiation of the cultured keratinocytes.

Measurement of TG-1 as an indicator of CE formation is disadvantageous, because it is an indirect measurement. The presence of TG-1 is just one of the required ingredients for the formation of CE. For instance, in the absence of CE precursor protein, CE will not be formed, even if TG-1 is present. Thus, the measurement of TG-1 may not be relied on exclusively to detect or quantify CE.

CE may be measured directly by counting (using a hemocytometer), by radioactive labeling, or by protein staining (also known as "dot blot" technique). The radioactive labeling presents a safety problem and is expensive and thus is not routinely used. Counting involves observing insolubilized protein, such as CE, under microscope and then counting manually the CE. This technique has a serious shortcoming, because it is time-consuming and labor-intensive: each CE must be individually detected and counted by looking through the microscope.

Monroe et al., "Quantitation of Cross-Linked Protein: An Alternative to Counting Cornified Envelopes as an Index of Keratinocyte Differentiation", Analytical Biochemistry, 199, pp. 25–28 (1991) describe a CE quantification method by dot blot technique, which separates cross-linked protein from soluble protein by collection of cross-linked protein on sheets of regenerated cellulose, binding of Coomasie blue to protein, and quantitation by scanning laser densitometry. Although the final step (detection and counting) is automated, the method is expensive due to the use of the expensive detection equipment-laser densitometer. Also, the sample preparation procedure is still extensive and time-consuming.

Colorimetric protein quantification methods based on measurement of absorbance (e.g. Lowry method) provide the most practical way to measure the protein concentration: they are fast, can be automated, and do not require expensive equipment. Such methods, however, traditionally require solubilized protein. See Lowry et al., "Protein Measurement With The Folin Phenol Reagent", Washington University School of Medicine, St. Louis, Mo., May 28, 1951, pp. 265–275. Unfortunately, CE is highly resistant to solubilization. See Sun et al., "Differentiation of the Epidermal Keratinocyte in Cell Culture: Formation of the Cornified Envelope", Cell, Vol. 9, pp. 511–521, December 1975 (Part 1), teaching that cornified cell envelope "is the most chemically resistant material of the stratum corneum," and that the "envelopes are insoluble in solutions of detergents, reducing agents and dilute alkali." According to Sun et al., CE remained insoluble even after heating in solutions of sodium dodecyl sulfate and beta-mercaptoethanol.

Bicinchoninic acid (hereinafter "BCA") is a known reagent used for absorbance-based measurement of protein. See Smith, U.S. Pat. No. 4,839,295. According to Smith, however, such protein is either solubilized or immobilized on an insoluble support such as agarose. See also Stich, "Determination of Protein Covalently Bound to Agarose Supports Using Bicinchoninic Acid", Analytical Biochemistry, 191, pp. 343–346 (1990).

The art does not disclose, however, the use of BCA for measuring of insoluble protein in general or for measurement of CE in particular. Measurement of insoluble protein differs from the measurement of protein bound to the insoluble support in that when soluble protein is bound to the insoluble support, a large part of the protein containing many available functional groups for binding is still free and is in solution, whereas the insoluble protein is entirely insoluble and most, if not all, of its functional groups are tied up in cross-linkages.

In actual fact, there was a prejudice in the state of the art which has until now dissuaded those skilled in the art from directing their attention towards using insoluble protein in a BCA assay. In addition to the general teaching of requirement to solubilize the protein in order to measure absorbance (see the Lowry article), see the Smith patent, teaching that the advantage of his BCA assay over the Lowry method is an improved protein solubilization in the BCA reagent (column 1, lines 29–30). See also Smith et al., "Measurement of Protein Using Bicinchoninic Acid", Analytical Chemistry, 150, pp. 76–85 (1985), again teaching the BCA assay for measurement of solubilized protein. See also Hill et al., "Protein Determination Using Bicinchoninic Acid in the Presence of Sulfhydryl Reagents", Analytical Biochemistry, 170, pp. 203–208 (1988), confirming that BCA method is to be used on the protein in solution. Therefore, it was very surprising to the present inventor that a BCA-based method of absorbance measurement is capable of measuring an insoluble protein.

The present invention meets a long felt need in the art for a simple and rapid in vitro system to quantify CE, in order to ascertain the state of keratinocyte differentiation. See the above-cited Monroe et al. article, published in 1991, after both the Smith patent and the Stich article have been published, and expressing the acute need for a practical CE detection method.

None of the previously cited art discloses the present method for measuring insoluble CE in an absorbance assay. Indeed, the present method overcomes the prejudice of the prior art against measuring insoluble protein, using BCA, in a colorimetric assay based on measurement of absorbance.

SUMMARY OF THE INVENTION

The present invention includes a method for measuring the concentration of cornified envelopes, the method comprising:

(a) removing soluble protein from cornified envelopes;

(b) preparing a suspension of the cornified envelopes obtained in step (a);

(c) adding to the suspension an alkaline aqueous reagent system containing $Cu^{2+}$ and the ion of bicinchoninic acid, whereupon a purple colored complex is formed;

(d) measuring the absorbance of the colored complex; and (e) determining the cornified envelope concentration by comparing the measured absorbance with the absorbance obtained on measurements of pellet suspensions containing a known number of cornified envelopes.

DETAILED DESCRIPTION OF THE INVENTION

The absorbance-based determination of CE utilizes the BCA reagent (ex Pierce) which is widely used for routine concentration measurement of soluble proteins. However, contrary to the teaching of the art which teaches solubilizing the protein with sodium dodecyl sulfate (SDS), adding the BCA reagent, and measuring the absorbance of the resultant sample, in the present invention solubilized protein part of the sample is discarded, and BCA is added to the insoluble part of the sample.

BCA Reagent

The BCA reagent is described in U.S. Pat. No. 4,839,295, incorporated by reference herein. The BCA reagent includes a source of $Cu_2+$ ion, e.g. 4% $CuSO_4$ and an alkaline solution of bicinchonic acid (i.e. bicinchonic acid salt) in a proportion of 1 part of $CuSO_4$ solution mixed with 100 parts of the alkaline BCA solution. The alkaline solution preferably contains sodium carbonate, sodium bicarbonate, sodium tartrate and 0.2N sodium hydroxide, most preferably 1% BCA, 2% $Na_2CO_3H_2$, 0.16% Na tartrate and 0.4% of NaOH.

CE sample preparation

Since CE remains insoluble after boiling in a solution of 4% SDS and 40 mM dithiothreitol (DTT), it may be purified from dissolved, uncornified cells of the epidermis. It is essential to remove the soluble proteins and DTT from CE preparation before the addition of the BCA reagent, because of the obvious interference. Preferably, the CE preparation is washed at least three times, most preferably at least four times, with SDS. The washing is performed by pelleting the CE fraction (e.g. by centrifuging), discarding the supernatant, adding SDS solution, vortexing with the SDS solution to obtain a suspension, and repeating the process.

Absorbance measurement

The absorbance measurement is conducted on the resultant pellet, which is free of soluble protein (see Example showing no reaction between BCA and the supernatant from the final wash). For the measurement the CE pellet is suspended on SDS solution, and the BCA reagent is added to the resultant suspension. A purple-color is produced upon the addition. The absorbance may be read at about 570 nm and the concentration of CE read of the standard curve.

The following specific examples further illustrate the invention, but the invention is not limited thereto.

EXAMPLE 1

Reagents

BCA reagent is from Pierce protein assay kit, SDS and DTT are from Sigma. Porcine skin is from Buckshire Corp., Perkasie, Pa.

BCA Analysis of CE

BCA CE assay reagent (Pierce product no. 23225, Pierce, Rockford, Ill.) was freshly prepared by mixing 50 volume of reagent A with 1 volume of reagent B. Reagent A contained 1000 ml of reagent containing sodium carbonate, sodium bicarbonate, bicinchoninic acid and sodium tartrate in 0.2N sodium hydroxide. Reagent B contained 25 ml of a solution containing 4% cupric sulfate.

Preparation of CE Fraction

The epidermis was separated from the dermis by pressing the epidermal side of 7 mm (unless otherwise specified) biopsies for 7 seconds with a heated aluminum cylinder and scraping with a scalpel. Subsequently, the epidermal sheets were dispersed into individual corneocytes by boiling in a solution consisting of 40 mM dithiothreitol (DTT) in 0.5 ml of 4% sodium dodecyl sulfate (SDS) solution for 30 min in microcentrifuge tubes at 100° C. The resulting samples were vortexed to dissociate the corneocytes. The corneocyte fraction was pelleted using a microcentrifuge with 14,000 rpm for 7 min. The resulting pellet was washed four times with 0.5 ml of 4% SDS to remove the soluble protein and DTT in order to obtain a CE fraction. The washing was performed by pelleting the CE fraction (i.e. by centrifuging), discarding the supernatant, adding 0.5 ml of 4% SDS solution, vortexing with the SDS solution to obtain a CE suspension, and repeating the process. The resulting CE fraction was resuspended in 0.5 ml fresh 4% SDS at the end of the washing procedure.

10 µl of the resulting suspension and 40 µl of 4% SDS solution were added to all wells of a 96-well plate adjacent to the row for standard curve. Then, 200 µl of the working BCA reagent was added to each well and the plate was incubated for 30 min at 37° C. in an oven. Absorbance at 570 nm was measured on Mr 7000 Dynatech plate reader. Number of cornified envelopes was determined by comparison with the standard curve.

CE suspension for standard curve

The number of corneocytes dispersed in the suspension was counted using a hemocytometer and phase-contrast microscopy. This preparation was used as stock suspension for plotting the standard curves which were then used for the measurement of unknown samples. The concentration of the stock suspension for standard curves ranged from 0–3000 CE/µl. Preparation of standards for the measurement of the number of CE in the unknown samples is given in Table I. The values for the standard curve are detailed in Table II. Aliquot of 50 µl of the diluted stock CE suspensions were used for BCA reaction.

TABLE 1

Preparation of BCA standard curve for cornified envelope assay

| Sample (#) | SDS (4%) (μl) | CE Stock Suspens'n (μl) | [CE] (#CE/μl) | Aliquot (μl) | BCA Reagent (μl) |
|---|---|---|---|---|---|
| 1 | 1000 | 0 | 0 | 50 | 200 |
| 2 | 980 | 20 | 50 | 50 | 200 |
| 3 | 920 | 80 | 200 | 50 | 200 |
| 4 | 840 | 160 | 400 | 50 | 200 |
| 5 | 760 | 240 | 600 | 50 | 200 |
| 6 | 680 | 320 | 800 | 50 | 200 |
| 7 | 600 | 400 | 1000 | 50 | 200 |
| 8 | 520 | 480 | 1200 | 50 | 200 |
| 9 | 440 | 560 | 1400 | 50 | 200 |
| 10 | 360 | 640 | 1600 | 50 | 200 |
| 11 | 280 | 720 | 1800 | 50 | 200 |
| 12 | 200 | 800 | 2000 | 50 | 200 |
| 13 | 120 | 880 | 2200 | 50 | 200 |
| 14 | 40 | 960 | 2400 | 50 | 200 |

TABLE II

Standard Curve For CE Assay Using BCA Reagent
n = 3

| CE/μl | 0 | 400 | 600 | 800 | 1000 | 1200 | 1400 | 1600 | 1800 | 2000 | 2200 | 2400 |
|---|---|---|---|---|---|---|---|---|---|---|---|---|
| Mean A570 nm | 0 | 0.39 | 0.51 | 0.61 | 0.71 | 0.79 | 0.91 | 0.99 | 1.07 | 1.12 | 1.21 | 1.31 |
| std. deviat'n | 0 | 0.025 | 0.006 | 0.029 | 0.017 | 0.018 | 0.003 | 0.013 | 0.019 | 0.004 | 0.025 | 0.007 |

R squared = 0.989 (the closer to 1, the more straight is the line).

EXAMPLE 2

This example evaluates BCA absorbance of CE pellet and of supernatants after each wash during the preparation of CE pellet. CE pellet was prepared from a 20 mm biopsy of piglet skin (3–4 weeks old). In accordance with the procedure described in Example 1, except that 1 ml of 4% SDS solution was used instead of 0.5 ml whenever mentioned in the procedure.

To remove DTT and soluble protein from the CE preparation, CE pellet (obtained by centrifugation at 14,000 rpm for 7 min) was washed four times with 4% SDS solution. Aliquot of 50 μl supernatant following each washing procedure was saved for BCA reaction and absorbance measurement. At the end of washes, the pellet was resuspended in 1 ml of fresh 4% SDS. BCA reaction was conducted on the supernatant from washes and the CE suspension at 37° C. for 30 min. Results that were obtained are summarized in Table III.

TABLE III

| Sample | SDS control | 1st wash | 2nd wash | 3rd wash | 4th wash | CE 10X diluted | CE suspension |
|---|---|---|---|---|---|---|---|
| A570 nm | 0.082 | 1.958 | 0.79 | 0.146 | 0.1 | 0.432 | 1.326 |

It can be seen from the results in Table III that the second, third and fourth wash solutions gave results similar to SDS control—no reaction with BCA, which means that most or all soluble protein and DTT was removed (compare to the 1st wash which gave a positive reaction with BCA). CE suspension, on the other hand, gave a strong reaction with BCA which could not be ascribed to soluble protein or DTT.

Absorbance values of about 1.3 or higher fall on the upper end of a standard curve. It is preferred to calculate CE concentration from absorbance values of lower than 1.3. Hence, 10× dilution of CE suspension was prepared to measure absorbance more accurately. From this absorbance value (0.432), CE/μl was calculated to be approximately 550.5 for a 20 mm biopsy. This value multiplied by 10 gave a CE/μl in the original sample (5,505).

EXAMPLE 3

This example compares CE concentration measured via CE assay procedure described above with qualitative evaluation of the number of cornified envelopes by observing the stratum corneum thickness via transmission electron microscopy (TEM).

TEM Procedure

Biopsies from piglet and adult porcine skin were dissected into 0.5 mm pieces and prefixed overnight at 4° C. in 2% glutaraldehyde, 2% formaldehyde, 200 mM Na Cacodylate and 1.4% sucrose, pH 7.4. Washed samples were postfixed in 1% osmium tetroxide for 2 hr at 4° C. After rinsing, the samples were dehydrated in a graded series of acetone, embedded in Spurr resin and baked at 60° C. in an oven. Processed tissue was ultramicrotomed into 50 nm thin sections. Stained sections were examined using a JEOL 1200EX transmission electron microscope.

The results obtained via a BCA assay of the present invention, after analyzing the CE suspension prepared as described in Example 1, are summarized in Table IV.

TABLE IV

BCA Assay Measurement of CE Number in Porcine Skin

| | Piglet (4 weeks old) CE suspension ×2 diluted | Adult (1 year old) CE suspension ×3 diluted |
|---|---|---|
| Absorbance (570 nm) (average of 6 measurements) | 0.556 | 0.946 |
| CE/μl | 814.6 | 1643.3 |
| std. deviation | 37.2 | 78.5 |
| CE/7 mm biopsy | (814.6 × 500 × 2) = 814597.5 | (1643.3 × 500 × 3) = 2465005 |
| n = 6 | | |

It can be seen from Table IV, that the piglet's (young pig) stratum corneum contained about three times fewer cornified envelopes than the adult pig's stratum corneum. This was confirmed by observing the thickness of the stratum corneum via TEM: piglet's stratum corneum was about three times thinner than the adult pig's stratum corneum. The thickness of stratum corneum is directly proportional to the number of CE present therein, given the same biopsy size.

In Table III, the CE concentration for piglet skin was obtained from a 2 cm biopsy, whereas in Table IV a 7 mm biopsy from a different piglet was analyzed. A much higher value for CE concentration in Table III was due to a larger biopsy area (314 mm² area for 2 cm biopsy vs. 38.5 mm² area for 7 mm biopsy). The difference in areas was approximately 8 times. The difference in CE concentration was approximately 7 times.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method for measuring the concentration cornified envelopes, the method comprising:

(a) preparing a pellet of cornified envelopes by removing soluble protein from cornified envelopes and washing the pellet with sodium dodecylsulfate;

(b) preparing a suspension of the cornified envelopes obtained in step (a);

(c) adding to the suspension an alkaline aqueous reagent system containing $Cu^{2+}$ and the ion of bicinchoninic acid, whereupon a purple colored complex is formed;

(d) measuring the absorbance of the colored complex; and (e) determining the cornified envelope concentration by comparing the measured absorbance with the absorbance obtained on measurements of pellet suspensions containing a known number of cornified envelopes.

2. The method of claim 1, wherein the washing is repeated at least three times.

3. The method of claim 1, wherein prior to step (a) a corneocyte pellet is prepared, the corneocyte pellet containing the soluble protein and the cornified envelopes.

* * * * *